United States Patent
Rakucewicz

(10) Patent No.: US 6,661,504 B2
(45) Date of Patent: Dec. 9, 2003

(54) FAILURE DETECTING OPTOELECTRONIC SENSOR

(76) Inventor: John Rakucewicz, 31 Burt Ave., Northport, NY (US) 11768

(*) Notice: Subject to any disclaimer, the term of this patent is extended or adjusted under 35 U.S.C. 154(b) by 0 days.

(21) Appl. No.: 10/163,669

(22) Filed: Jun. 6, 2002

(65) Prior Publication Data

US 2003/0030790 A1 Feb. 13, 2003

Related U.S. Application Data

(63) Continuation of application No. 09/035,079, filed on Mar. 4, 1998, now abandoned.
(60) Provisional application No. 60/040,620, filed on Mar. 4, 1997.

(51) Int. Cl.$^7$ .................................. G01N 21/41
(52) U.S. Cl. .................. 356/128; 356/136; 356/137
(58) Field of Search ................ 356/128, 135–137; 250/577, 574, 575

(56) References Cited

U.S. PATENT DOCUMENTS

| | | | | |
|---|---|---|---|---|
| 4,354,180 A | * | 10/1982 | Harding | 340/619 |
| 4,809,551 A | * | 3/1989 | Grossiord | 73/327 |
| 5,399,876 A | * | 3/1995 | LaClair | 250/577 |

* cited by examiner

Primary Examiner—Michael P. Stafira
(74) Attorney, Agent, or Firm—Wechsler & Wechsler, P.C.; Lawrence I. Wechsler

(57) ABSTRACT

An optoelectronic liquid sensor indicates failure of operative components therein. The sensor includes a light source, a light detector, and a transparent probe which functions as a primary liquid sensing prism. The transparent probe is of a suitable configuration permitting internal reflection of light transmitted therethrough from the light source, along a primary light path for reception by the light detector, when the light-impinged surface of the primary prism is in air. When the same surface of the probe is submersed in or exposed to liquid, light from the light source traveling along the primary light path is refractively transmitted into the liquid, and therefore almost no light reaches via the primary light path. A secondary light path is provided, along which a fraction of the light from the light source is also transmitted via internal reflection within a transparent body to the light detector. This is accomplished conveniently, for example, by a secondary prism which is isolated from exposure to surrounding media, and which is trapezoidally configured in cross-section and optically polished to internally reflect the received light. Therefore, as long as the sensor components are operable, a portion of light transmitted by the light source and internally reflected along the secondary light path is consistently received by the light detector.

20 Claims, 3 Drawing Sheets

FAILURE DETECTING OPTOELECTRONIC SENSOR

CROSS REFERENCE TO RELATED APPLICATIONS

This is a continuation of application Ser. No. 09/035,079, filed Mar. 4, 1998 entitled FAILURE DETECTING OPTOELECTRONIC SENSOR now abandoned, which in turn claims the benefit of U.S. Provisional Application No. 60/040,620 filed Mar. 4, 1997 entitled FAILURE DETECTING OPTOELECTRONIC SENSOR.

BACKGROUND OF THE INVENTION

The present invention relates to optoelectronic sensors, and more particularly optoelectronic liquid level sensors and detectors which provide indication of sensor component failure irrespective of environmental conditions.

Optoelectronic liquid level sensors are well known in the art, and are typically used to detect the presence or absence of a liquid or for sensing whether the level of liquid in a vessel has risen above or fallen below a predetermined depth. Optoelectronic sensors are primarily used as point type liquid detectors, although they are sometimes used conversely as point type air bubble detectors, since they are capable of distinguishing between the different media directly in contact with surface portions thereof.

Operation of such devices utilizes principles of internal reflection governed by the differences of refractive indices between an optically transparent probe portion, and the surrounding medium. The probe portion is commonly provided in the form of cylinder having an optically polished conical tip. A light beam is directed through the probe portion in the direction of the conically formed tip. The probe is made of a material having an index of refraction such that the angle at which the light impinges the surface of the conical tip from the interior of the probe is greater than the critical angle when the probe surface is exposed to air, whereby virtually all of the light is internally reflected. When exposed to liquid, the critical angle, determined as a known function of the ratio of the indices of refraction of the probe material and the surrounding media (i.e. gas or liquid) with which it is in contact, is greater than the angle of incidence, resulting in transmission of the impinging light beam passed internally through the probe outward of the conical tip, refracted into the surrounding medium. A light detector, positioned to receive the light that is internally reflected when the probe is exposed to air (or other gas with similar index of refraction), provides means for producing a measurable circuit parameter responsive to an amount of light received thereby, by which "wet" and "dry" conditions can be determined. For convenience, a light source and a light detector are placed side by side and spaced apart in a location at the circular face of the cylindrical portion of the probe, and the conical tip configured at a 90° angle, such that the angle of incidence is approximately 45°, and the beam from the light source is reflected back to the light sensor along a return path approximately parallel wit the incident beam.

In practice, such optoelectronic sensors comprise a light emitting diode (L.E.D.) as the light source, a phototransistor (P.T.) as the light detector, and a housing to protect the operational components of the sensor and to facilitate mounting thereof. Sometimes, for convenience, the prism and housing are machined or molded as one piece from suitable material, such as transparent plastic.

The drawback of such sensors is that should the operational components, including the light source and/or the detector, fail, there is no practical way of distinguishing between such failure and the presence of liquid. This is particularly problematic in applications where it is important to know when liquid has dropped below a certain level, since the probe is ordinarily not responding to the internal light beam when immersed and will not indicate any change upon light failure, giving a continuously false reading that liquid is still present at point of measurement. Also, in applications where the sensor is not easily accessible, determination of whether the components are operational by removal and testing thereof is impractical. In such cases it is impossible to distinguish between a reading generated by presence of liquid and product failure.

It would therefore be desirable to be able to monitor the functionality of a liquid sensor without adding additional circuitry or wiring to it which would otherwise contribute to the cost of such device and decrease its statistical reliability because of higher component counts and the number of extra solder joints required. Furthermore, since these optoelectronic liquid sensors typically have integrated circuit means for producing a voltage on a single output lead representative of the condition of the sensor, it would also be desirable to permit such failure-detecting monitoring strictly by determination of a single output voltage level, or other conveniently measurable circuit parameter. Ideally, such fail-safe feature would be included in an optoelectronic sensor arrangement in a manner obviating elaborate structural configuration of the various components which might complicate manufacture or limit a range of suitable material from which they are fabricated.

SUMMARY OF THE INVENTION

Accordingly, it is an object of the invention to provide an optoelectronic liquid sensor which overcomes the drawbacks of the prior art.

It is a further object of the invention to provide an optoelectronic liquid sensor in which continuous monitoring of the functionality of the various operational components of a liquid sensor may be implemented.

It is a still further object of the invention to provide an optoelectronic liquid sensor in which failure detection of the various components may be determined by conversion of a measurable circuit parameter into an output level representative of the conditions of wet, dry and sensor failure, such as for example, production of three discrete voltage levels corresponding to each of the sensor states.

Yet another object of the invention is to provide an optoelectronic sensor which integrates a conversion circuit as part of a self-contained sensor which producing a discrete voltage signal on an output line.

It is yet another object of the invention to provide such a failure detecting feature in an optoelectronic sensor in a simple, reliable and cost effective manner.

Briefly stated, the present invention provides an optoelectronic liquid sensor providing facilitated failure detection of the various operative components contained therein. The sensor includes a light source, a light detector, and a transparent probe which functions as a primary liquid sensing prism. The transparent probe is of a suitable configuration permitting internal reflection of light transmitted therethrough from the light source, along an internally reflected primary light path for reception by the light detector, when the light-impinged interior surface of the primary prism is in air. When the light impinged surface of the probe is submersed in or exposed to liquid, light from the light source traveling along the primary light path, instead of being internally reflected, is refractively transmitted into the liquid, and therefore almost no light reaches via the primary light path. In addition to the primary light path, a secondary light path is provided in the sensor, along which a fraction of the light from the light source is analogously transmitted via internal reflection within a transparent body to the light detector. This is accomplished conveniently, for example, by a secondary prism which is isolated from ambient exposure such that it is consistently exposed to an air or gaseous environment, and which is trapezoidally configured in cross-section and optically polished to internally reflect the received light. Alternatively, such secondary light path may be provided by structural configuration of the transparent probe which functions also as the primary liquid sensing prism. In either embodiment, as long as the sensor components are operable, a portion of light transmitted by the light source and internally reflected along the secondary light path is consistently received by the light detector. The light detector is wired as part of a suitable circuit, the design of which is at least partially dependent upon the nature of the type detector, for detecting changes in the level of the particular circuit parameter altered as a result of the particular detector's exposure to light levels, for example a change in current, and also including means for converting such parameter value into output values representative of three discrete levels corresponding to conditions of, wet, dry and sensor failure, respectively.

In accordance with these and other objects of the invention, there is provided an embodiment of a sensor in accordance with the invention which includes a light source conveniently in the form of a light emitting diode, a phototransistor light detector, and a transparent probe which functions as a primary liquid sensing prism. A secondary prism, which is trapezoidally configured in cross-section, internally reflects a portion of light output from the L.E.D. along a secondary light path to be received by the phototransistor.

According to a further feature of the invention, there is further provided another embodiment in which the primary light prism as described above is specially configured to present secondary structure enabling transference of light via internal reflection along a secondary light path within the single transparent probe.

The present invention also includes the above embodiments wherein, an entire sensor body is fashioned in one piece, and includes external structure facilitating mounting in an application. Alternatively, the components may be mounted in a separately provided housing of suitable material and construction.

In an advantageous embodiment, each of the above embodiments may be combined with a circuit integral with the sensor, such that external conversion of a circuit parameter influenced by a level of light received by the detector is obviated. Conveniently, this is provided as a printed circuit housed directly in the sensor, and encapsulated.

The above, and other objects, features and advantages of the present invention will become apparent from the following description read in conjunction with the accompanying drawings, in which like reference numerals designate the same elements.

THE PRIOR ART

Figure 1:
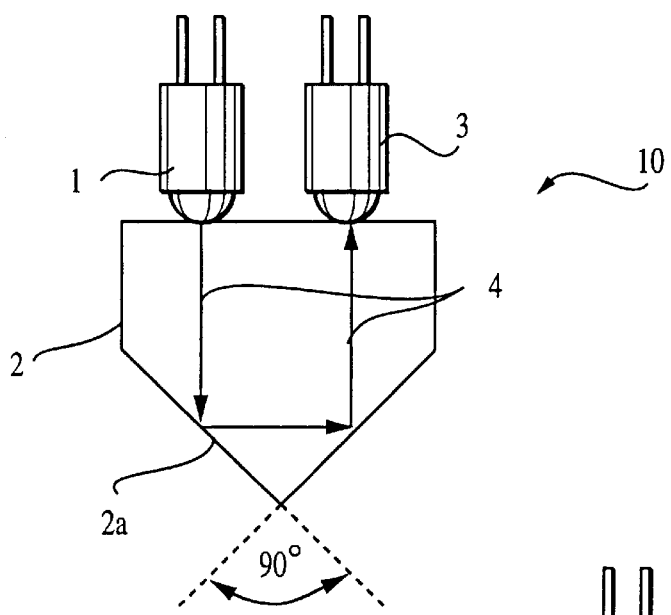
FIG. 1 is a simplified schematic operational view of a conventional prismatic optoelectronic liquid sensor, a probe surface of which is shown in contact with air.
Figure 2:
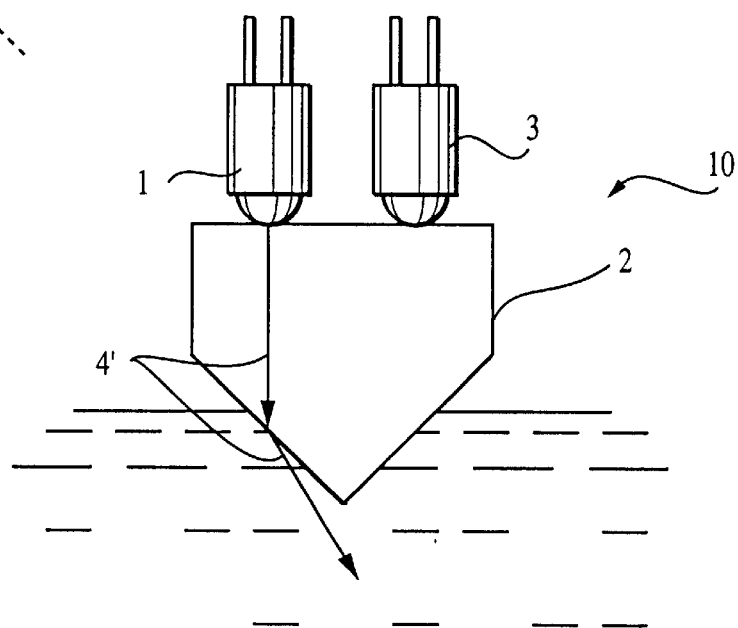
FIG. 2 is a simplified schematic operational view of a conventional prismatic optoelectronic liquid sensor, a probe surface of which is shown in contact with a liquid medium.

Operation of a prior art optoelectronic sensor without failure detection capabilities will now be described with reference to a typical arrangement depicted schematically in FIGS. 1 and 2, in which the sensor is shown in contact with air (or gaseous environment) and a liquid, respectively. For clarity of illustration, and since it is not generally deemed an operation element of the sensor, the housing is not depicted. Prior art sensor, generally designated 10, comprises an L.E.D. 1, a prism 2, and a phototransistor 3. Light is transmitted from L.E.D. 1 into prism 2. Prism 2, as shown, has a cylindrical body tapered at an end thereof to present a conical lower portion 2a, and has an optically polished surface such that when the reflecting surfaces of the prism's conical portion 2a are in air, as shown in FIG. 1, light will follow a light path 4 as shown, and be almost totally internally reflected back into phototransistor 3. If however the reflecting faces of prism 2 are in contact with a liquid having a sufficiently high refractive index, the emitted light will be almost totally refracted into the liquid along a light path 4' (indicated by arrows) since the angle of incidence for light striking the interior of conical portion 2a is greater than the critical angle of prism 2 under submerged conditions.

For purposes herein, a condition or state of a sensor will be referred to by the term "dry" when in contact with a gaseous environment, and by the term "wet" when in contact with a liquid.

Figure 3:
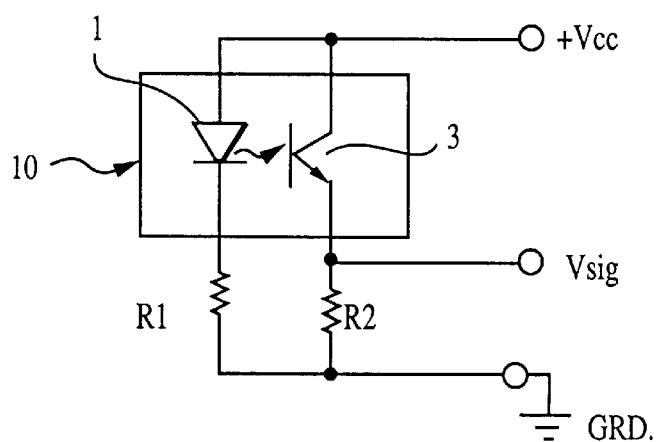
FIG. 3 is a schematic diagram of a typical detection circuit for providing operational output from the sensor of FIGS. 1 and 2 in the form of a voltage level.

When wired into a suitable detection circuit, for example of the type shown in FIG. 3, an output voltage indicates the wet/dry condition of sensor 10. As shown, the emitter voltage ($V_{sig}$) will go "high" when the sensor is dry (air) and "low" when the sensor is wet (liquid). Conversely, the opposite output (high/wet, low/dry) can also be created by the use of any one of a number of other conventional, as well as non-conventional, schemes. A properly constructed and operational sensor in a circuit as described above will exhibit voltage levels at the emitter typically as follows. (Assume $V_{cc}$=15 VDC).

$V_{sig}$

| "DRY" | "WET" |
|---|---|
| +14.8 | +.008 |

It is understood that these voltages will be reversed when using a suitable converse scheme as discussed above. For purposes herein, the illustrated example only will be addressed, and all conclusions drawn for this approach are deemed valid for the converse approach by substituting the words "wet" for "dry", and "dry" for "wet".

In the dry state, a significant amount of the light emitted from L.E.D. 1 is reflected back to phototransistor 3, saturating it. Thus, current flows out of the base/emitter junction of phototransistor 3 to ground through a resistor R2. The voltage drop across resistor R2 is the signal voltage $V_{sig}$. The value of resistor R2 is typically selected to be significantly high so that the moderate amount of current produced by the saturated phototransistor 3 in the dry state produces a voltage ($V_{sig}$) close to the power supply voltage. Conversely, in the wet state, almost no light reaches the phototransistor. With only a minuscule amount of "dark" current flowing, the voltage drop across resistor R2 is essentially zero.

As shown in the following Table 1, sensor 10 wired as shown in FIG. 3 fails to distinguish between a functional and a failed sensor in the wet condition. (input voltage $+V_{cc}$ is 15 VDC). Note that the actual value of $V_{sig}$, i.e. 0.008 volts is represented by "0" in Table 1, shown below.

TABLE 1

| L.E.D. | P.T. | State | Vsig | Sensor |
|---|---|---|---|---|
| GOOD | GOOD | DRY | 14.8 | FUNCTIONAL |
| GOOD | GOOD | WET | 0 | FUNCTIONAL |
| GOOD | BAD | DRY | 0 | NON-FUNCTIONAL |
| GOOD | BAD | WET | 0 | NON-FUNCTIONAL |
| BAD | GOOD | DRY | 0 | NON-FUNCTIONAL |
| BAD | GOOD | WET | 0 | NON-FUNCTIONAL |
| BAD | BAD | DRY | 0 | NON-FUNCTIONAL |
| BAD | BAD | WET | 0 | NON-FUNCTIONAL |

It is often necessary, and even critical, to know whether an optoelectronic sensor of this type has failed electronically within a system. It is important, therefore, to detect a dysfunctional sensor regardless of the sensor's condition, i.e. wet or dry, at the time of its failure.

DESCRIPTION OF THE PREFERRED EMBODIMENT

Figure 4:
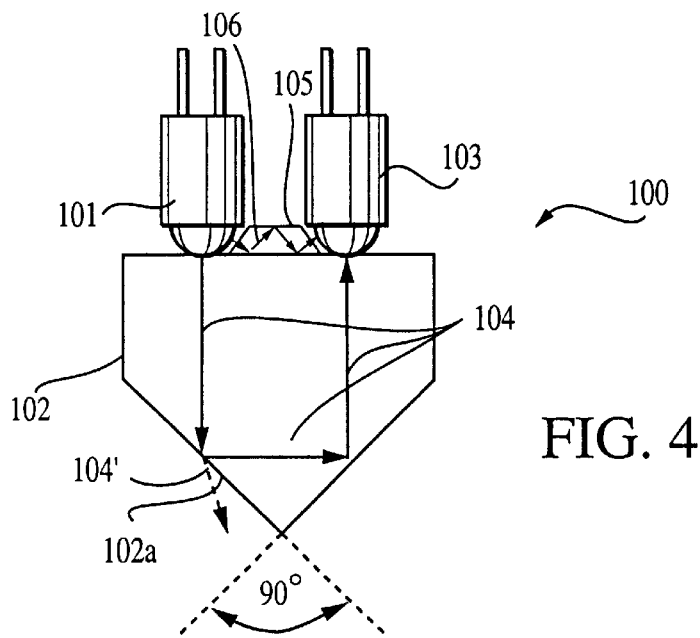
FIG. 4 is an simplified schematic of a sensor in accordance with an embodiment of the invention.

Referring to the figures, and in particular FIG. 4, a sensor in accordance with an embodiment of the invention is depicted, generally designated 100, and which enables facilitated failure detection of the various operational components, as detailed below. Sensor 100 includes a light source, conveniently a light emitting diode (L.E.D.) 101, a phototransistor (P.T.) 103, and a primary liquid sensing prism 102. Like prior art prism 2 discussed earlier herein, primary prism 102 is advantageously optically polished, and is of a suitable configuration permitting internal reflection of light emitted from L.E.D. 101 along a primary light path 104 for reception by P.T. 103, when primary prism 102 is in air (or gas having sufficiently low index of refraction). This is conveniently accomplished, for example, by providing prism 102 with a 90° conical portion 102a, as shown. Although not actually shown in contact with liquid, when conical portion 102a of prism 102 (or analogous internally reflective surfaces of other suitably configured prism embodiments) is submersed in liquid, light from L.E.D. 101 traveling along primary light path 104 is refractively transmitted into the liquid (along a refracted path 104', shown in the figure as a dotted arrow) by virtue of its higher index of refraction, in a manner analogous to that described with reference to the prior art sensor 10, and therefore almost no light reaches P.T. 103 via primary light path 104.

In order to provide a primary objective in accordance with embodiment of the present invention, i.e. change in a measurable circuit parameter enabling production of three discrete output voltage levels, each corresponding to one of wet, dry, and sensor failure irrespective of the prior two states, a secondary light path 106 is provided, along which light from L.E.D. 101 is transmitted to P.T. 103. This is accomplished in the depicted embodiment by a secondary prism 105 which is trapezoidally configured in cross-section and optically polished to internally reflect light as shown by the arrows representing secondary light path 106. Secondary prism 105, which is disposed above primary prism 102 between L.E.D. 101 and P.T. 103, is shielded from liquid contact. Therefore, as long as the sensor is operable, a portion of light transmitted by L.E.D. 101 and reflectively transferred along secondary light path 106 is constantly received by P.T. 103, irrespective of wet/dry conditions. P.T. 103 is a type thereof capable of producing a variable current output proportional to the intensity of light received at its base when wired in a suitable circuit, for example of the type described with reference to the prior art and schematically depicted in FIG. 3, in which prior art sensor 10 is replaced with sensor 100 (and L.E.D. 101 and P.T. 103 replacing L.E.D. 1 and P.T. 3). As such, the signal voltage $V_{sig}$ produced by phototransistor 103 is equal to the voltage produced by the sum total of the voltages produced by the light which strikes it along each of primary light path 104 and secondary light path 106. Expressed as an equation:

$$V_{sig} = V_{(L1)} + V_{(L2)}$$

where:
L1 designates the portion of light travelling along primary light path 104, and L2 designates the portion of light travelling along secondary light path 106.

Therefore, as long as sensor 100 is properly operational, $V_{(L2)}$ will remain a constant positive value regardless if whether primary liquid sensing prism 102 is wet or dry. Under the same conditions, $V_{(L1)}$ will either be a constant positive value if sensor 100 is dry and light is internally reflected along primary light path 104, or essentially zero if light from L.E.D. 101 is refracted into surrounding liquid. If either L.E.D. 101 or P.T. 103 fails, both voltage components $V_{(L1)}$ and $V_{(L2)}$, and hence $V_{sig}$, will be zero volts.

Table 2 indicates how three discrete voltage levels, one for each of the three conditions, i.e. good/wet, good/dry, and dead can be produced by sensor 100. In the table, "a" and "b" signify arbitrary positive voltage levels for each of $V_{(L1)}$ and $V_{(L2)}$ respectively, and "0" signifies zero volts.

TABLE 2

| L.E.D. | P.T. | State | $V_{(L1)}$ | $V_{(L2)}$ | $V_{sig}$ | Sensor |
|---|---|---|---|---|---|---|
| GOOD | GOOD | "DRY" | a | b | a + b | FUNCTIONAL |
| GOOD | GOOD | "WET" | 0 | b | b | FUNCTIONAL |
| GOOD | BAD | "DRY" | 0 | 0 | 0 | NON-FUNCTIONAL |
| GOOD | BAD | "WET" | 0 | 0 | 0 | NON-FUNCTIONAL |
| BAD | GOOD | "DRY" | 0 | 0 | 0 | NON-FUNCTIONAL |
| BAD | GOOD | "WET" | 0 | 0 | 0 | NON-FUNCTIONAL |
| BAD | BAD | "DRY" | 0 | 0 | 0 | NON-FUNCTIONAL |
| BAD | BAD | "WET" | 0 | 0 | 0 | NON-FUNCTIONAL |

Figure 5:
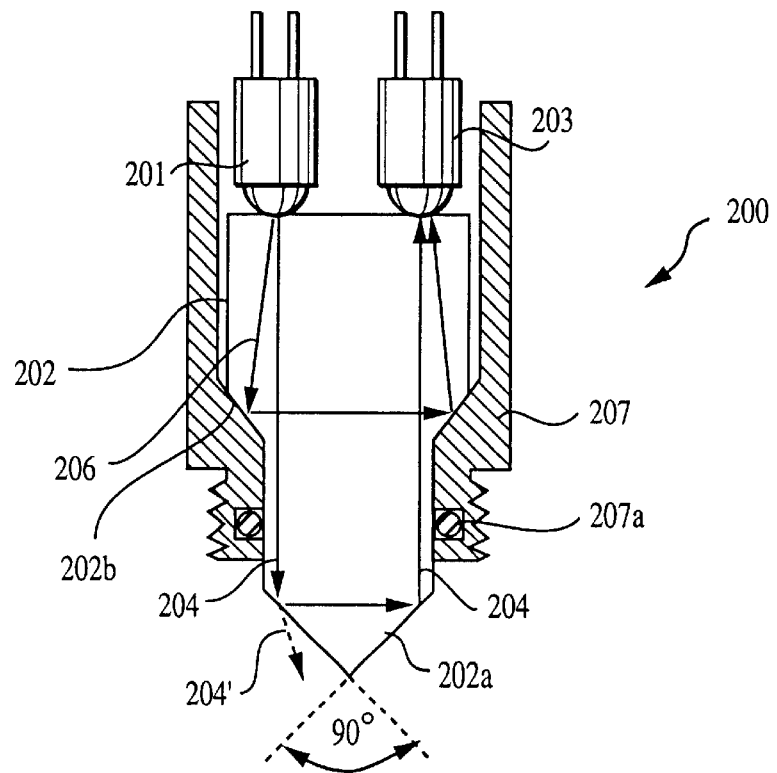
FIG. 5 is an simplified schematic of a sensor in accordance with another embodiment of the invention.

Turning now to FIG. 5, another embodiment of a sensor in accordance with the invention is shown, generally designated 200. Sensor 200 comprises an L.E.D. 201, a prism 202 and a P.T. (phototransistor) 203. Prism 202 is optically polished, and presents a shape having a conical lower sensing portion 202a configured conveniently at a 90° angle, and a stepped upper portion 202b presenting reflective surfaces with an appropriate angles of incidence to internally reflect light as shown by the representative arrows when greater that the critical angle determined by the ambient medium. By virtue of such shape, and assuming dry conditions and an operative sensor, light from L.E.D. 201 travels along multiple internal light paths, i.e. a primary light path 204 defined by light internally reflected from conical lower sensing portion 202a, and a secondary light path 206 consisting of light reflected off stepped upper portion 202b, as indicated in the figure.

A housing 207 provides means for shielding upper stepped portion 202b from contact with liquid, conveniently in the form of an o-ring seal 207a. As such, a portion of light emitted from L.E.D. 201 travels along secondary light path 206 and is constantly transmitted to P.T. 203, irrespective of wet/dry conditions, in a manner analogous to that of the previously described embodiment, however without the requirement of a secondary prism. Similarly, a portion of light is transmitted along primary light path 204 to P.T. 203 when conical lower sensing portion 202a is dry, but is refracted almost completely along a refracted path 204' (shown by a dotted arrow) when exposed to liquid, and therefore never reaches P.T. 203 when wet. When wired in a circuit as described with reference to the previous embodiment, sensor 200 functions analogously to sensor 100 depicted in FIG. 4, producing three discrete voltage level outputs representative of the various states of good/wet, good/dry, and dead.

Figure 6:
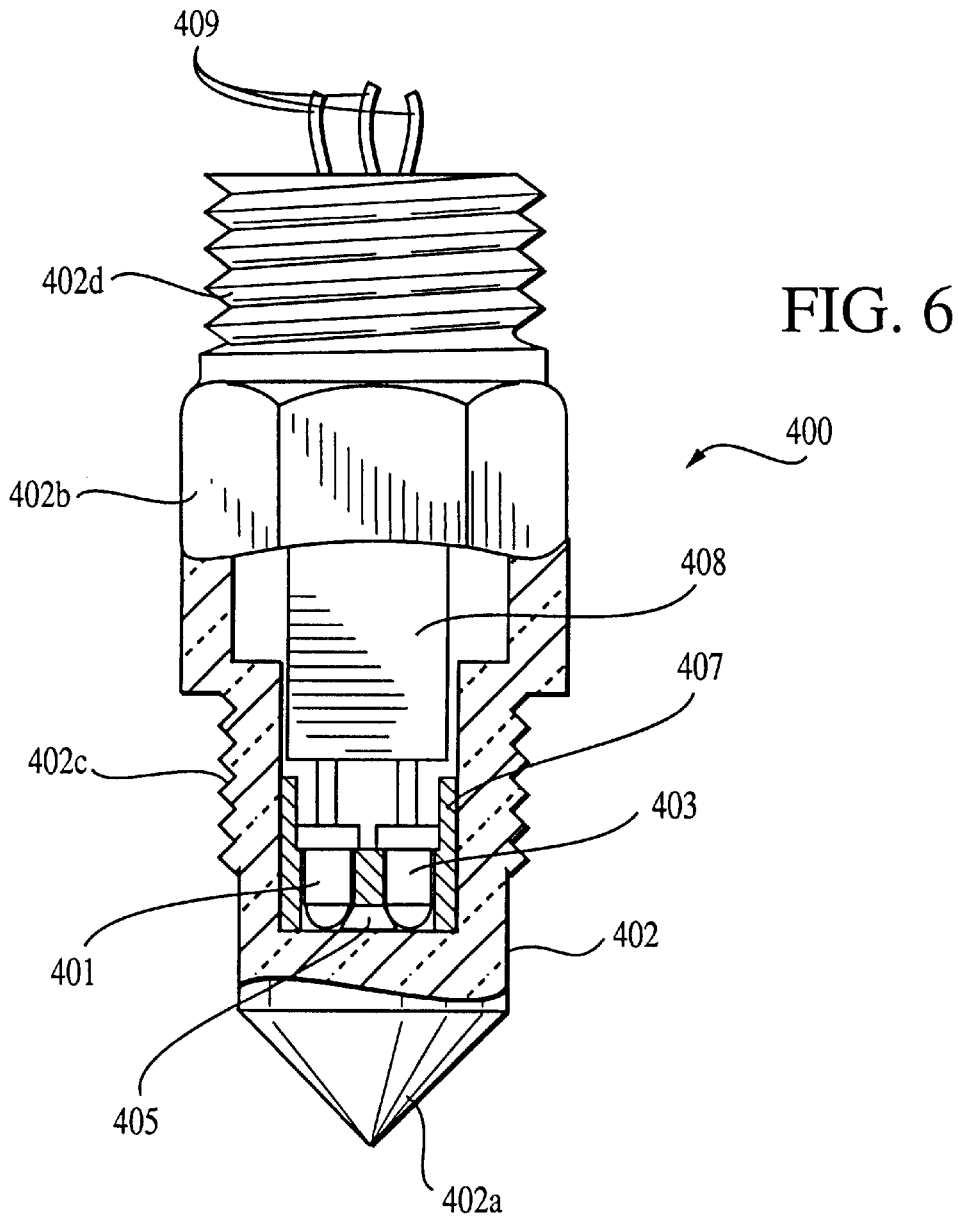
FIG. 6 is side elevational view shown in partial cross-section of a practical embodiment of the sensor of FIG. 4.

By utilizing internal reflection to transmit light through both a volatile primary and a consistent secondary light path, a resultant sensor may be made simply and economically, with excellent reliability. The above described examples, as well as those not specifically depicted yet deemed broadly embraced within the scope of the invention as contemplated, are easily implemented in a practical setting. Referring for example to FIG. 6, a sensor embodying the features generally described with reference to the sensor type of FIG. 4 is depicted, the sensor generally designated 400. Sensor 400 includes an L.E.D. 401 and a P.T. (phototransistor) 403 as active elements. A transparent probe 402 includes structure presenting a prism portion which includes a conical portion 402 which defines the internally reflected primary light path in a manner consistent with that described above herein, and concomitantly integral housing structure presenting threaded portions 402c and 402d, and wrench flats 402b. Suitable materials from which transparent probe 402 may be fabricated includes any number of plastics having appropriate indices of refraction and light transmissiveness, for example, polysulfone. Where the sensor is used in applications in which it is exposed to corrosive substances, the material will be selected taking into account its chemical resistance to the particular substance. A secondary prism 405 is provided, carried conveniently on an insert 407 which also includes L.E.D. 410 and P.T. 403 mounted thereto. The insert is receivable in suitable position within a bore in transparent probe 402. A circuit to perform the function of that of FIG. 3, conveniently provided as a printed circuit board 408, may be advantageously encapsulated within transparent probe 402 using, for example, known epoxy encapsulation methods, along with the other active elements. Three leads 409 exit sensor 400 and are connected to circuit 408, representing ground, supply voltage and output voltage, respectively.

Figure 7:
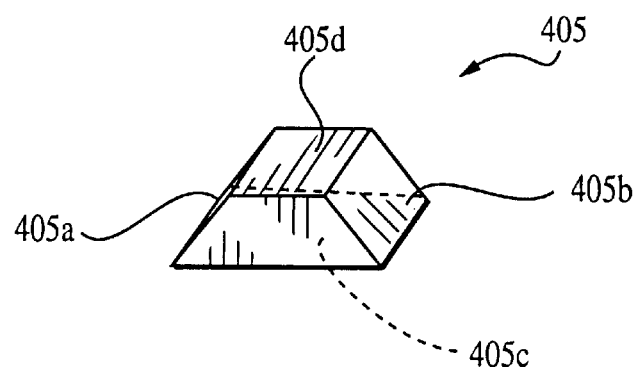
FIG. 7 is an detailed perspective view of a trapezoidally configured prism for providing a secondary light path in the embodiment depicted in FIG. 6.

Turning to FIG. 7, secondary prism 405 is shown in detail. Secondary prism 405 is configured as a three dimensional trapezoid, and includes a light inlet surface 405a and a light outlet surface 405b aligned when installed adjacent L.E.D. 401 and P.T. 403, respectively. Light is internally reflected at an angle from surface 405c, and where the width of the trapezoidal shape is too great to allow only one reflection, back and forth diagonally between surface 405c and an opposed surface 405d until exiting light outlet surface 405b.

It is noted that although the illustrative examples are directed to use of prism structure for creating an internally reflected light path, a fiber-optic or other structure providing means for internal reflection may be implemented without departure from the intended scope herein. In addition, many other prism shapes, sizes and configurations not specifically depicted are contemplated, the inventive concept not being limited to specific spacial characterization. Also, although the phototransistor used for convenience as the light detector in the described examples converts light into a measurable circuit parameter in the form of a variable control of current flow between collector and emitter, other type light detectors which convert light into other circuit parameters, including measurable changes in resistance, capacitance, inductance or production of a direct variable current output, can be used without departure from the invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A failure detecting optoelectronic sensor of the type which distinguishes between presence of gas and liquid in an immediate environment in which it is positioned, comprising:

a probe portion, by which light emitted by a light source is selectively guided along a primary light course to impinge a light detector, conditioned upon a nature of the immediate environment in which it is positioned, said probe portion being comprised of a light conductive substance presenting an outer surface which is exposed to said immediate environment, said light conductive substance having an index of refraction and being structurally configured to internally reflect light generated by a light source from an interior of said outer surface thereby conducting the light along said primary light course to impinge the light detector when said outer surface is in contact with air, and to refract at least a substantial portion of said light into a surrounding thereof outwardly through said outer surface when said outer surface is in contact with a liquid; and a secondary light transmitting portion comprised of another light conductive substance and configured such that a supplementary portion of said light generated by said light source is conducted along a secondary light course via internal reflection within said another light transmissive substance to impinge said light detector irrespective of the nature of said immediate environment in which said optoelectronic sensor is positioned.

2. An optoelectronic sensor according to claim 1, further comprising: a light source; and a light detector.

3. An optoelectronic sensor according to claim 1, wherein said light conductive substance and said another light conductive substance are substantially a same material.

4. An optoelectronic sensor according to claim 2, wherein said light source and said light detector are spaced apart at a common end of said probe portion, said primary light course reflecting from an internal surface of said outer surface portion distant from said common end.

5. An optoelectronic sensor according to claim 1, wherein said probe portion and said secondary light transmitting portion are integrated structural portions of a common prism.

6. An optoelectronic sensor according to claim 1, wherein said transparent probe portion is comprised of a primary prism via which said at least the portion of light from said light source is directed along said primary light course, and said secondary light transmitting portion is comprised of a secondary prism via which said secondary portion of the light from said light source is directed along said secondary light pat.

7. An optoelectronic sensor according to claim 6, wherein said primary prism has a shape defined collectively by a generally cylindrical portion and an approximately 90° conical portion lying on a common longitudinal axis, said light source and said light detector being spaced apart at an end of said cylindrical portion, said conical portion including said outer surface portion.

8. An optoelectronic sensor according to claim 6, wherein:
said secondary prism has a trapezoidal shape in cross-section; and
said secondary prism is positioned between said light source and said light detector at said common end of said primary prism.

9. An optoelectronic sensor according to claim 7, wherein said conical portion is optically polished at least over an area portion thereof.

10. An optoelectronic sensor according to claim 6, wherein said primary prism is formed integrally with a housing, said housing having a longitudinally-formed bore extending to said common end of said prism, each of said light source, said light detector and said secondary prism being received within said bore.

11. An optoelectronic sensor according to claim 10, wherein said bore is sealed by encapsulation.

12. An optoelectronic sensor according to claim 1, wherein at least one of said light conductive substance and said another light conductive substance comprises polysulfone.

13. An optoelectronic sensor, comprising:
a light source;
a light detector;
a probe comprised of a light conductive substance presenting a first outer surface portion and a second outer surface portion, said first outer surface portion being contactable with said immediate environment;
said light conductive substance having an index of refraction and being structurally configured to internally reflect at least a portion of light generated by the light source from a first internally reflective region corresponding to an interior of said first outer surface portion thereby conducting the light along a primary light course to impinge the light detector when said first outer surface portion is in contact with air, and to refract at least a substantial portion of said at least the portion of light into a surrounding thereof outwardly through said first outer surface when said first outer surface portion is in contact with a liquid; and
said light conductive substance being further configured such that a secondary portion of the light generated by said light source is conducted along a secondary light course via internal reflection within said light transmissive substance from a second internally reflective region corresponding to an interior of said second outer surface portion to impinge said light detector irrespective of a nature of said immediate environment in which said optoelectronic sensor is positioned.

14. An optoelectronic sensor according to claim 13, wherein said light source includes a light emitting diode.

15. An optoelectronic sensor according to claim 13, wherein said light detector includes a phototransistor.

16. An optoelectronic sensor according to claim 13, wherein said light source and said light detector are located at an end of said probe, said light source introducing light codirectionally with a longitudinal axis of said probe, said second internally reflective region being formed by a stepped region located concentrically outward of said first internally reflective region and longitudinally spaced apart therefrom.

17. An optoelectronic sensor according to claim 16, further comprising a housing partially enclosing said probe, said stepped region being insulated from contact with said immediate environment by a seal between the housing and the probe located in a longitudinal position of the probe lying between said stepped region and said first internally reflective region.

18. A method of detecting failure of at least one of a light source and a light detector in an optoelectronic sensor of the type which distinguishes between presence of gas and liquid in an immediate environment in which it is positioned, and in which a primary portion of light from the light source is selectively guided along a primary light course to impinge the light detector when the immediate environment is dry, and at least a substantial portion of the primary portion of light being diverted from the primary light course when the immediate environment is wet in such manner that the at least a substantial portion of light does not impinge the light detector when the optoelectronic sensor is exposed to liquid, the method comprising:
guiding a secondary portion of light from the light source along a secondary light course via internal reflection within a light transmissive substance to impinge said light detector irrespective of a nature of said immediate environment in which said optoelectronic sensor is positioned;
measuring a level of light impinging the light detector; and
determining a functional failure of the optoelectronic sensor based upon said level of light.

19. A method according to claim 18, further comprising insulating a surface portion of said light transmissive substance from contact with said immediate environment.

20. A method according to claim 18, wherein said primary and said secondary light courses are directed within a common prism.

* * * * *